United States Patent [19]

Pilgram et al.

[11] 4,168,153
[45] Sep. 18, 1979

[54] CYCLOALKANECARBOXANILIDE DERIVATIVE HERBICIDES

[75] Inventors: Kurt H. G. Pilgram; Richard D. Skiles, both of Modesto, Calif.

[73] Assignee: Shell Oil Company, Houston, Tex.

[21] Appl. No.: 876,594

[22] Filed: Feb. 10, 1978

Related U.S. Application Data

[63] Continuation-in-part of Ser. No. 761,515, Jan. 21, 1977, abandoned.

[51] Int. Cl.$^2$ .................. C07C 103/19; A01N 9/12; A01N 9/14; A01N 9/20
[52] U.S. Cl. .......................... 71/118; 71/98; 71/103; 260/556 B; 260/557 R; 260/562 P
[58] Field of Search ............ 260/556 B, 557 R, 562 P; 71/98, 103, 118

[56] References Cited

U.S. PATENT DOCUMENTS

| | | | |
|---|---|---|---|
| 3,211,544 | 10/1965 | Dubrovin | 71/118 |
| 3,328,156 | 6/1967 | Hopkins | 71/118 |
| 3,407,056 | 10/1968 | Schwartz | 71/118 |
| 3,484,485 | 12/1969 | Schwartz | 260/557 R |
| 3,660,486 | 5/1972 | Thiele | 260/562 P |
| 3,753,679 | 8/1973 | Singhal | 71/98 |
| 4,090,865 | 5/1978 | Baker | 260/562 P X |

FOREIGN PATENT DOCUMENTS

| | | | |
|---|---|---|---|
| 749581 | 10/1970 | Belgium | 71/118 |
| 1921840 | 11/1969 | Fed. Rep. of Germany | 260/562 P |
| 1141183 | 1/1969 | United Kingdom | 260/557 R |
| 1246885 | 9/1971 | United Kingdom | 260/557 R |
| 1255161 | 12/1971 | United Kingdom | 260/557 R |
| 1344735 | 1/1974 | United Kingdom | 71/98 |

OTHER PUBLICATIONS

Martin et al., CA 74:12853w (1971).
Esso, CA 79: 18343e (1973).

*Primary Examiner*—Thomas A. Waltz

[57] ABSTRACT

Certain cycloalkanecarboxanilide derivatives are useful as herbicides.

6 Claims, No Drawings

CYCLOALKANECARBOXANILIDE DERIVATIVE HERBICIDES

CROSS-REFERENCE TO RELATED APPLICATIONS

This application is a continuation-in-part of Ser. No. 761,515, filed Jan. 21, 1977, now abandoned.

BACKGROUND OF THE INVENTION

1. Field of the Invention

This invention relates to cycloalkanecarboxanilide derivatives, their use as herbicides and to herbicidal compositions containing these cycloalkanecarboxanilides.

2. Summary of the Invention

The present invention is directed to a new class of compounds which are useful to control plant growth. This class of compounds is characterized as amides derived from a substituted cycloalkanecarboxylic acid and certain 3,4-disubstituted anilines.

DETAILED DESCRIPTION OF THE INVENTION

The present invention is directed to new compounds, particularly useful as herbicides, having the formula

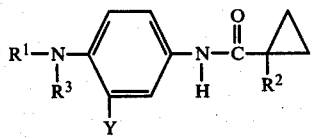
(I)

wherein

Y is a halogen atom of atomic number 9 to 35, inclusive, $NO_2$, or the group $-Z_p$-alkyl in which the alkyl portion contains from 1 to 6 carbon atoms and can be substituted by one or more halogen atoms of atomic number 9 to 35, inclusive;

Z is O, S, SO or $SO_2$;

$R^1$ is an alkyl group of from 1 to 6 carbon atoms, or a cycloalkyl or a (cycloalkyl)alkyl group having from 3 to 7 carbon atoms in the ring;

$R^2$ is an alkyl or alkoxy group of from 1 to 6 carbon atoms or a halogen atom having an atomic number of 9 to 35, inclusive;

$R^3$ is a hydrogen atom or an alkyl or cycloalkyl group of up to 6 carbon atoms; and p is 0 or 1.

The compounds shown in formula I above are derivatives of substituted-cyclopropane carboxylic acids. Examples were $R^2$ in the formula is alkyl include methyl, ethyl, propyl, n-butyl and the like or where $R^2$ is alkoxy include methoxy, ethoxy or propoxy and the like or where $R^2$ is a halogen atom, fluorine, chlorine or bromine.

As a general rule, the compounds preferred because of their herbicidal properties are those compounds of formula I wherein $R^2$ is methyl. The compounds wherein $R^2$ is chlorine or methoxy are also very active.

The group Y can be chlorine, bromine or fluorine, $NO_2$, trifluoromethyl, trifluoromethoxy, methyl, ethyl, methylsulfonyl, trifluoromethylsulfonyl and the like.

Preferred because of their herbicidal properties are compounds of formula I wherein Y is trifluoromethyl. Compounds wherein Y is methyl, ethyl, chlorine, bromine or $NO_2$ are also very active.

$R^1$ can be straight-chain, or preferably branched-chain, alkyl such as methyl, ethyl, isopropyl, isobutyl, secondary-butyl, tertiary-butyl, isoamyl and the like, or cyclopropyl, cyclohexyl, methylcyclopropyl, cyclopropylmethyl and the like.

Compounds wherein $R^1$ is alkyl of 1 to 4 carbon atoms or cycloalkyl are generally preferred. Especially active are those compounds wherein $R^1$ is branched-chain alkyl such as isopropyl or tert-butyl and the like. Ethyl, methyl and cyclopropylmethyl derivatives and ring alkylated forms are also highly active. Variations in activity of course depend on the individual combinations of $R^1$, $R^2$, $R^3$ and Y.

$R^3$ is a hydrogen atom, an alkyl group such as methyl, ethyl, isopropyl, n-propyl, tert-butyl and the like, or cycloalkyl such as methylcyclopropyl. $R^3$ is preferably a hydrogen or alkyl group such as methyl or n-propyl.

Examples of species contemplated when Y is trifluoromethyl include the following:

4'-(tert-butylamino)-3'-(trifluoromethyl)-1-methylcyclopropanecarboxanilide

4'-(propargylamino)-3'-(trifluoromethyl)-1-methylcyclopropanecarboxanilide

A preferred subclass because of their herbicidal properties are those compounds of formula I wherein Y is $CF_3$, $R^3$ is hydrogen or alkyl such as methyl, propyl and the like, $R^1$ is alkyl of 1 to 4 carbon atoms, especially isopropyl, tert-butyl or n-propyl, and $R^2$ is methyl.

Compounds of formula I wherein Y is $NO_2$ are a useful subclass of the invention due to their relative easy and low cost of preparation as well as to their herbicidal properties. Preferred because of their herbicidal properties are those compounds where Y is $NO_2$ and $R^1$ is alkyl of 2 to 4 carbon atoms. Especially useful compounds appear to be those wherein $R^1$ is isopropyl or tert-butyl and $R^3$ is hydrogen or alkyl and $R^2$ is methyl.

Examples of species contemplated when Y is alkyl include the following:

4'-(isopropylamino)-3'-methyl-1-methylcyclopropanecarboxanilide

4'-(tert-butylamino)-3'-methyl-1-methylcyclopropanecarboxanilide

4'-((1-methylcyclopropyl)amino)-3'-methyl-1-methylcyclopropanecarboxanilide

Examples of species contemplated when Y is halogen include the following:

4'-(dimethylamino)-3'-bromo-1-methylcyclopropanecarboxanilide

4'-(diethylamino)-3'-bromo-1-methylcyclopropanecarboxanilide

4'-(isopropylamino)-3'-bromo-1-methylcyclopropanecarboxanilide

4'-(tert-butylamino)-3'-bromo-1-methylcyclopropanecarboxanilide

Cycloalkylcarboxanilides, I, can be prepared according to the following sequence of reactions:

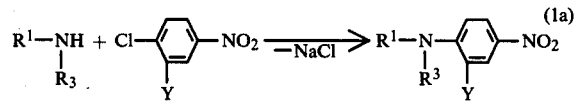
(1a)

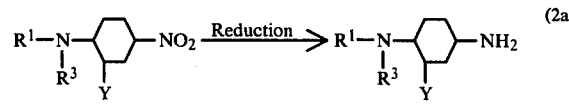
(2a)

-continued

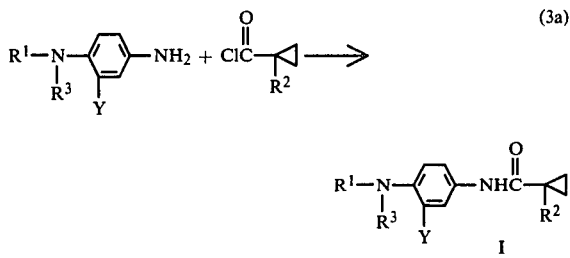

The appropriate amine is allowed to react with 3-substituted-4-chloronitrobenzene to give 3,4-disubstituted nitrobenzene; step (1a). In step (2a) the 3,4-disubstituted nitrobenzene is reduced to give the corresponding aniline. In step (3a) the aniline and a cycloalkylcarboxylic chloride are allowed to react to give the desired cycloalkylcarboxanilide, I.

Reaction (1a) is readily conducted by mixing the reactants in a solvent such as an alcohol, dimethyl sulfoxide or dimethylformamide at room temperature, for example up to 150° C.

The reduction of the 3,4-disubstituted nitrobenzenes, step (2a) is readily carried out in boiling water containing iron filings and up to 5% of acetic or hydrochloric acid. However, any of numerous reduction techniques that reduce an aromatic nitro group to amino are applicable here (see R. Schroter and F. Moller in Methoden der Organische Chemie. "Houben-Weyl", Vol. 11, 1, part IV, p. 341-731, Georg Thiene Verlag, Stuttgart (1957)).

The acylation reaction (3a) is conducted by treating the 3,4-disubstituted aniline with a cycloalkylcarboxylic chloride in a suitable solvent such as ether, tetrahydrofuran, benzene, toluene or hexane in the presence of one molar equivalent of an organic or inorganic base that can serve as acceptor for the hydrogen chloride formed in the reaction. Organic bases such as tertiary amines (pyridine, triethylamine, collidine, N,N-dimethylaniline, ethyldiisopropylamine) or inorganic bases ($Na_2CO_3$, $NaHCO_3$, $K_2CO_3$, $CaCO_3$) may be used to trap the hydrogen chloride formed during acylation.

The cycloalkylcarboxylic chlorides used in the reaction or simple esters from which they can be generated are generally known in the art as for example in U.S. Pat. Nos. 3,277,171, 3,211,544 and South African application 64/1283. The 1-fluorocycloalkylcarboxylic chlorides can be readily prepared by treating 1-chlorocycloalkylcarboxylic acid ethyl ester with potassium fluoride at elevated temperatures optionally in the presence of solvents and/or phase transfer catalysts and converting the ester to acid chloride in a known manner. The 1-bromocycloalkylcarboxylic chlorides can be prepared by bromination of cycloalkylcarboxylic chlorides under refluxing conditions in a nitrogen atmosphere.

The compounds of the invention, for example, 4'-(isopropylamino)-3'-(trifluoromethyl)-1-methylcyclopropanecarboxanilide, have been found to be useful for controlling undesirable plant growth. That is, certain members of the class have been found to be herbicidally effective against a wide range of plant species. Others of the class are effective only against a limited number of plant species and are considered to be selective herbicides. Some of the compounds exhibit a high degree of herbicidal activity in the control of a variety of economically important species of grasses and broad-leaved weeds. Some of the compounds are particularly useful as selective herbicides for use in certain important crops.

The invention includes plant growth regulating compositions comprising a carrier or a surface-active agent, or both a carrier and a surface-active agent, and, as active ingredient, at least one compound of Formula I. Likewise the invention also includes a method of controlling plant growth which comprises applying to the locus an effective amount of a compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates for example natural silicas such as diatomaceous earths; magnesium silicates, for example, talcs; magnesium aluminum silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 1–5% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally granules will contain ½–25% by weight toxicant and 0–10% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5–5% w of dispersing agents, 1–5% of surface-active agent, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the compounds of this invention comprises applying a compound of Formula I, ordinarily in a composition of one of the aforementioned types, to a locus or area to be protected from undesirable plant growth. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 pounds per acre of the compound used in this invention will be satisfactory.

EXAMPLES

The manner in which the compounds of this invention can be prepared is illustrated in the following examples, which demonstrate the preparation of typical species of the invention. In these examples, the identities of all compounds, intermediates and final, were confirmed by elemental analysis, and infrared and nuclear magnetic spectral analyses. The examples are for the purpose of illustration only and should not be regarded as limiting the invention in any way.

EXAMPLE 1

4'-(Isopropylamino)-3'-(trifluoromethyl)-1-methylcyclopropanecarboxanilide (a) Preparation of N-isopropyl-4-nitro-2-(trifluoromethyl)benzenamine To a solution of 45 g of 3-(trifluoromethyl)-4-chloronitrobenzene in 150 ml of DMSO was added 13 g of isopropylamine. The mixture was heated at 80°–90° C. for two hours, poured over ice water, acidified and filtered. The filter cake was dried to yield 49.6 g of product; m.p. 35°–36° C.

(b) Preparation of 4-(isopropylamino)-3-(trifluoromethyl)benzenamine

About 565 ml of 5% acetic acid was heated to 90° C. and 49.6 g of 1 (a) above was added. 123 g of iron powder was added portionwise. The resulting mixture was refluxed for 1 hour, then filtered while hot. The filtrate was cooled and extracted with ether. The ether extract was washed with 10% aqueous sodium bicarbonate and then with water, dried and concentrated to give 38.7 g (89%) of product as a light amber oil.

(c) Preparation of 4'-(isopropylamino)-3'-(trifluoromethyl)-1-methylcyclopropanecarboxanilide To a solution of about 19 g of 1 (b) above in 150 ml of tetrahydrofuran and 8.8 g of triethylamine was added 10.3 g of 1-methylcyclopropanecarboxylic acid chloride dropwise over 5 minutes at 25°–64° C. The reaction mixture was stirred, refluxed for 30 minutes, poured over ice water, and extracted with ether. The ether extract was dried and concentrated, and the residue was crystallized from ether/petroleum ether to give 22 g (84%) of grey solid; m.p. 100°–102° C.

EXAMPLES 2–12

In the manner described in the above Examples, additional cyclopropanecarboxanilides listed in Table 1 were prepared.

Table 1

Cyclopropanecarboxanilides

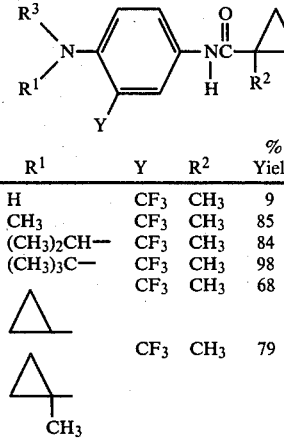

| Ex. | R³ | R¹ | Y | R² | % Yield | Melting Point, °C. |
|---|---|---|---|---|---|---|
| 2 | H | H | | CF₃ | CH₃ | 9 | 136–141 |
| 3 | CH₃ | CH₃ | | CF₃ | CH₃ | 85 | 89–91 |
| 4 | CH₃ | (CH₃)₂CH— | | CF₃ | CH₃ | 84 | 98–100 |
| 5 | H | (CH₃)₃C— | | CF₃ | CH₃ | 98 | 105–108 |
| 6 | H | △ | | CF₃ | CH₃ | 68 | 126–128 |
| 7 | H | △-CH₃ | | CF₃ | CH₃ | 79 | 120–122 |
| 8 | C₃H₇ | C₃H₇ | | CF₃ | CH₃ | 68 | 74–76 |
| 9 | H | (CH₃)₂CH— | | NO₂ | CH₃ | 2 | 172–174 |
| 10 | H | (CH₃)₃C— | | NO₂ | CH₃ | 4 | 211–214 |

Table 1-continued

Cyclopropanecarboxanilides

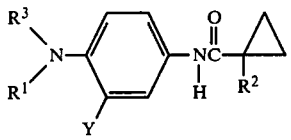

| Ex. | R³ | R¹ | Y | R² | % Yield | Melting Point, °C. |
|---|---|---|---|---|---|---|
| 11 | C₃H₇ | C₃H₇ | NO₂ | CH₃ | 31 | 77-79 |
| 12 | H | (CH₃)₂CH— | Br | CH₃ | 26 | 89-90 |
| 13 | CH₃ | (CH₃)₂CH— | CF₃ | Cl | 65 | 55-57 |
| 14 | CH₃ | (CH₃)₂CH— | CF₃ | C₂H₅ | 38 | oil |
| 15 | CH₃ | CH₃ | Br | CH₃ | 16 | 99-100 |
| 16 | CH₃ | CH₃ | CH₃ | CH₃ | 58 | 98-99 |
| 17 | H | (CH₃)₂CH— | CH₃ | CH₃ | 27 | 84-85 |

EXAMPLE OF HERBICIDAL ACTIVITY

The pre-emergence herbicidal activity of the compounds of the invention was evaluated by planting seeds of garden cress, downey brome, wild mustard (or sicklepod) and velvet leaf in test tubes, nominally measuring 25×200 millimeters, containing soil treated with the test compound at the rates of 0.1 and 1 mg per tube designated in Table I at Rates I and II, respectively. The planted soil was held under controlled conditions of temperature, moisture, and light for 13 to 14 days. The amount of germination and growth in each tube were evaluated on a 0 to 9 scale, 0 rating indicating no effect, 9 death of seedlings or no germination.

The post-emergence activity of the compounds of this invention was evaluated by spraying 7-day old crabgrass plants, 10-day old pigweed plants, 7-day old downey brome plants, 10-day old wild mustard (or 7-day old sicklepod) and 10-day old velvet leaf plants to runoff with a liquid formulation of the test compound at the rates of 0.62 milliliter of an 0.05% solution designated Rate I in Table I, and 0.56 milliliter of an 0.5% solution designated Rate II in Table I. The sprayed plants were held under controlled conditions for 10 to 11 days and the effect of the test compound was then evaluated visually, the results being rated on the 0 to 9 scale described above.

The results of the pre- and post-emergence tests are summarized in Table I.

TABLE I

| | RESULTS OF THE HERBICIDE ACTIVITY SCREEN | | | | | | | | | | | | | | | | | | |
|---|---|---|---|---|---|---|---|---|---|---|---|---|---|---|---|---|---|---|---|
| | PRE-EMERGENCE (SOIL) | | | | | | | | POST-EMERGENCE (FOLIAR) | | | | | | | | | | |
| | Garden Cress | | Downey Brome | | Wild Mustard | | Velvet Leaf | | Crab-grass | | Pig-weed | | Downey Brome | | Wild Mustard | | Velvet Leaf | |
| Example | I | II | I | II | I | II | I | II | I | II | I | II | I | II | I | II | I | II |
| 1 | 8 | 8 | 2 | 6 | 9 | 9 | 2 | 8 | 5 | 5 | 9 | 9 | 2 | 5 | 8 | 9 | 9 | 9 |
| 2 | 3 | 7 | 1 | 2 | 7 | 8 | 3 | 8 | 0 | 0 | 0 | 5 | 0 | 0 | 0 | 2 | 0 | 5 |
| 6 | 2 | 8 | 0 | 0 | 9 | 9 | 0 | 7 | 0 | 7 | 3 | 8 | 1 | 1 | 7 | 9 | 6 | 9 |
| 3 | 8 | 9 | 3 | 8 | 9 | 9 | 5 | 9 | 9 | 9 | 8 | 9 | 5 | 7 | 9 | 9 | 8 | 9 |
| 7 | 2 | 8 | 0 | 3 | 0 | 9 | 2 | 6 | 8 | 9 | 9 | 9 | 5 | 7 | 9 | 9 | 9 | 9 |
| 4 | 2 | 8 | 0 | 0 | 9 | 9 | 3 | 5 | 9 | 9 | 9 | 9 | 8 | 9 | 9 | 9 | 9 | 9 |
| 5 | 8 | 9 | 0 | 0 | 9 | 9 | 6 | 7 | 9 | 9 | 9 | 9 | 8 | 9 | 9 | 9 | 9 | 9 |
| 8 | 2 | 4 | 0 | 0 | 0 | 2 | 2 | 2 | 8 | 9 | 8 | 9 | 2 | 9 | 9 | 9 | 8 | 9 |
| 9 | 8 | 8 | 4 | 5 | 8 | 8 | 5 | 6 | 8 | 8 | 8 | 8 | 3 | 3 | 3 | 9 | 9 | 9 |
| 11 | 0 | 9 | 0 | 0 | 0 | 0 | 0 | 0 | 8 | 9 | 6 | 9 | 5 | 8 | 7 | 9 | 2 | 9 |
| 14 | 3 | 6 | 0 | 0 | — | — | 0 | 0 | 0 | 6 | 0 | 7 | 0 | 4 | — | — | 0 | 7 |
| 10 | 5 | 5 | 0 | 0 | — | — | 0 | 0 | 2 | 2 | 2 | 5 | 0 | 0 | — | — | 4 | 4 |
| 15 | 7 | 7 | 9 | 9 | 6 | 7 | 9 | 9 | 3 | 9 | 9 | 9 | 9 | 9 | 9 | 9 | 9 | 9 |
| 16 | 5 | 7 | 2 | 5 | 0 | 8 | 0 | 7 | 6 | 8 | 5 | 8 | 0 | 7 | 3 | 9 | 0 | 7 |
| 17 | 2 | 9 | 0 | 6 | 0 | 9 | 0 | 6 | 2 | 3 | 3 | 7 | 0 | 2 | 5 | 9 | 0 | 5 |

In many instances the compounds of the invention possess a selective action against weeds in crop plant cultures. Control of weeds in soybean crops is an example of the selective herbicidal activity of 4'-(isopropylamino)-3'-(trifluoromethyl)-1-methylcyclopropanecarboxanilide.

The above species and/or other species of the invention have likewise shown post-emergence, and in some cases, pre-emergence selective activity for wheat, peanuts, grain sorghum, cotton, rice, corn, alfalfa or the like.

We claim:

1. A compound of the formula

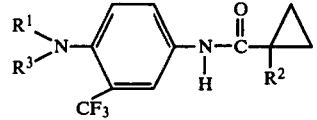

wherein $R^1$ is n-propyl, isopropyl or tert-butyl; $R^2$ is methyl and $R^3$ is hydrogen, methyl or n-propyl.

2. A compound according to claim 1 wherein $R^1$ is isopropyl and $R^3$ is a hydrogen atom.

3. A compound according to claim 1 wherein $R^1$ is tert-butyl and $R^3$ is a hydrogen atom.

4. A compound according to claim 1 wherein $R^1$ is isopropyl and $R^3$ is methyl.

5. A herbicidal composition comprising a herbicidally effective amount of a compound according to claim 1 and at least one surface-active agent or carrier.

6. A method for controlling undesirable plant growth at a locus to be protected which comprises applying to the locus to be protected a herbicidally effective amount of a compound according to claim 1 or a composition thereof.

* * * * *